United States Patent
Bick

Patent Number: 5,159,640
Date of Patent: Oct. 27, 1992

[54] APPARATUS FOR CARRYING OUT HYPNOTHERAPIES

[76] Inventor: Claus Bick, Flesenland-Bick-Klinik, Dahn, Fed. Rep. of Germany

[21] Appl. No.: 465,515

[22] Filed: Jan. 16, 1990

Related U.S. Application Data

[63] Continuation of Ser. No. 165,773, Mar. 9, 1988, abandoned.

[30] Foreign Application Priority Data

Mar. 24, 1987 [CH] Switzerland ............... 01110/87

[51] Int. Cl.$^5$ ............... H04B 3/00; H04M 3/42
[52] U.S. Cl. ............... 381/77; 381/80; 455/3.1; 455/53.1
[58] Field of Search ............... 381/74, 77, 80, 81, 381/85; 455/2, 3, 5, 6, 53, 56, 66; 340/825.06, 825.07

[56] References Cited

U.S. PATENT DOCUMENTS

| | | | |
|---|---|---|---|
| 3,200,516 | 8/1965 | Parker | 381/77 |
| 3,541,915 | 11/1970 | Rhodes | 381/77 |
| 3,594,505 | 7/1971 | Price | 381/77 |
| 3,784,717 | 1/1974 | Okamoto | 381/77 |
| 3,795,769 | 3/1974 | Nowka | 381/77 |
| 3,826,871 | 7/1974 | Kraemer | 381/80 |
| 3,882,538 | 5/1975 | Lowe | 381/77 |
| 4,717,343 | 1/1988 | Densky | 358/181 |

Primary Examiner—Tommy P. Chin
Attorney, Agent, or Firm—Herbert Dubno

[57] ABSTRACT

An apparatus for hypnotherapy which has a plurality of headphone stations for the respective subjects and a central station which can switch a control group therapy sound reproducer to all of the headphone stations for initiating, deepening and withdrawal from hypnosis stages. The headphone stations are associated with individual sound reproducers for the individual suggestion programs and a microphone can be selectively connected at the central station. A rushing water sound generator can be selectively connected to the modulation stages of the central station or the individual loudspeaker stations.

1 Claim, 1 Drawing Sheet

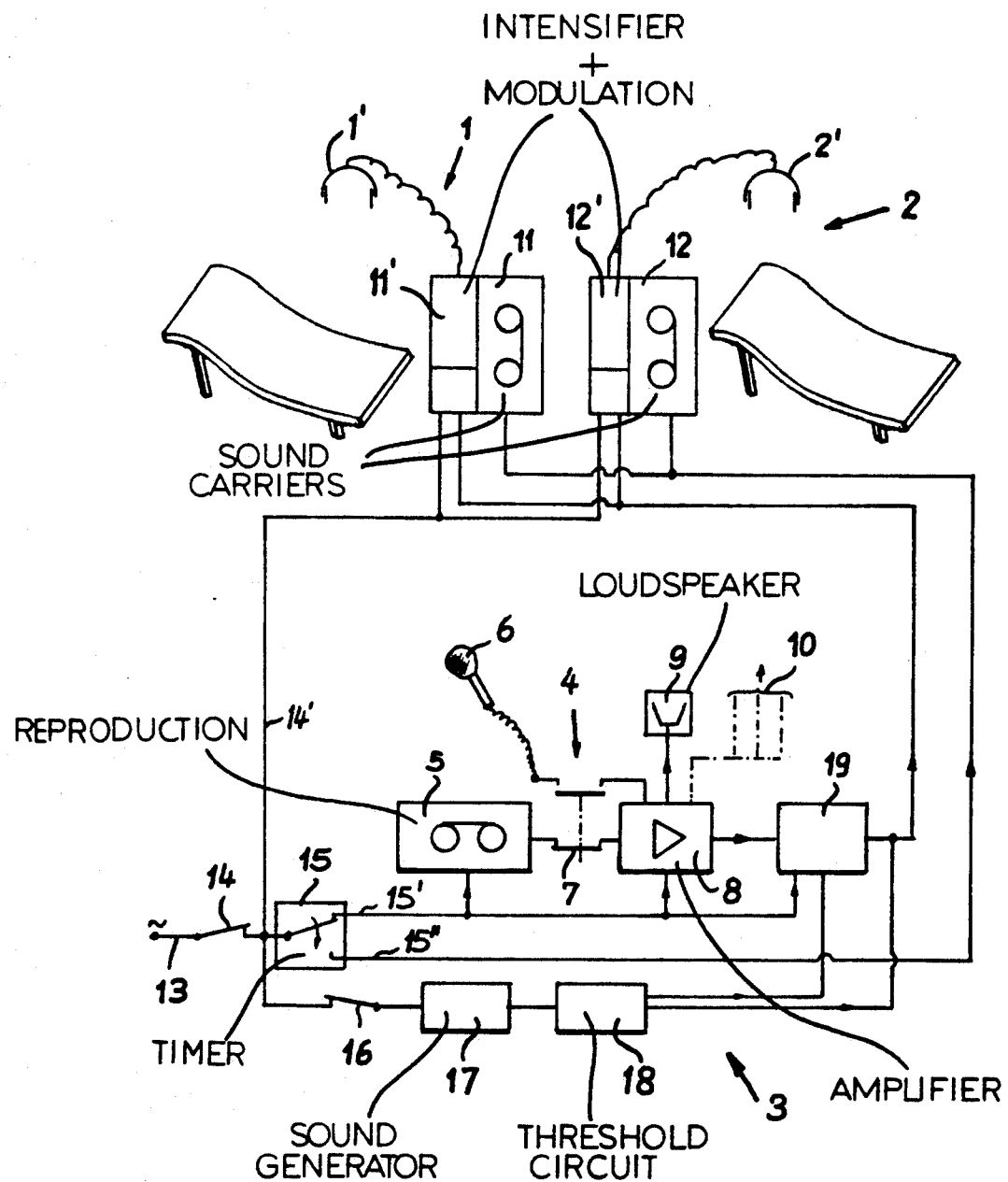

APPARATUS FOR CARRYING OUT HYPNOTHERAPIES

This is a continuation of co-pending application Ser. No. 07/165,773 filed on Mar. 9, 1988 now abandoned.

FIELD OF THE INVENTION

The present invention relates to an apparatus for carrying out hypnotherapies.

BACKGROUND OF THE INVENTION

Psychogenic-therapy methods using suggestive treatment with a therapeutic and prophylactic character are gaining increasingly in importance, since there exists a very high probability of a positive influencing of the subconscious Through this treatment, in a deep physically and psychically (hypnotic) relaxed state—which is in itself already of great therapeutic effect—, the negative mental (disturbing) factors, which are fixed in the subconscious mind and evoke (subconsciously) misguided behavior, are replaced suggestively by positive, mental-motivating elements.

Notwithstanding the necessity for different individual, treatments for executing the aforementioned exchange, it is, in order to relieve the therapist in charge, unavoidable and possible to carry out at least the first stage of maintaining and deepening of the relaxation condition by means of appropriate equipment.

OBJECT OF THE INVENTION

It is thus the object of the present invention to provide an apparatus that permits hypnotheraphy in the preceding sense.

SUMMARY OF THE INVENTION

This is achieved according to the invention in that a plurality of headphone stations, which permit the therapeutic treatment of several patients simultaneously, and which are alternately switchable between a control part, common to all headphone stations, with a sound-reproduction stage for the introduction of the hypnosis in a group or the return out of the hypnosis, and, in each case, a sound-carrier reproducer for conducting individual suggestion.

With such means, the physician conducting the therapy can henceforth simultaneously reach via sound carrier or microphone several patients wearing headphones, and exercise a suggestive influence on these patients for the introduction and deepening of the hypnosis. Between the introduction or deepening of the hypnosis and further deepening or returning, a common intermediate switching-over to the sound-carrier reproducer, individually allocated to each headphone, can take place, so that each patient receives individual suggestion, which has previously been compiled and prepared with the therapist.

Experiments have led to exceptional results in this connection, particularly when the sound carriers for the individual suggestion formulas are spoken by the same therapist who also speaks the introduction, deepening and return formulas. When taken into consideration, then, that on the one hand a single hypnotherapy session takes about 1 hour, namely, about 5 minutes for greeting and seating the patient, about 20 minutes for the hypnotic introduction, about 5 minutes for the individual suggestion and again about 30 minutes for deepening and returning, and on the other hand, that, with such an apparatus according to the invention, up to 12 and more patients can be attended to simultaneously, the significance of such an apparatus becomes obvious both for therapists and patients.

In a further embodiment of the multi-functional hypnotic apparatus, said sound-reproduction stage for group therapy comprises at least one sound-carrier reproducer as well as a microphone which may be switched on alternately. This enables the therapist to play the introduction, deepening and returning programs alternatively from sound carriers, as tape, CD or the like, or to speak via microphone. Preferably, secondary devices are provided to immediately counter any disturbances in the arrangement.

Furthermore, it is of advantage to make the microphone alternately connectable with a room loudspeaker and/or station loud-speakers and/or the headphones of said stations, which further ameliorates the individual operation of the arrangement by the therapist.

It has been found that certain sounds, as in particular the rushing of the sea, act sedatively to a high degree. To utilize this here, it is moreover intended to allocate an appropriate sound-generating unit to said common control part, which should be selectively switched on and alternately switched over to an intensifier and modulation stage of said individual sound-carrier reproducers or to a modulation stage for group therapy downstream of said sound-reproduction stage in order to bring the rushing of the sea by itself as well as also for the group and individual suggestion superimposed onto the headphones. Preferably, the sound-generating unit is, moreover, a controllable, time-controlled threshold stage downstream of said sound-generating unit in order to adjust the volume of the rushing sound to the course of the therapy.

Moreover, additional echo and/or resonance stages can be connectable.

For a time-controlled, automatic course of a therapy session, it is moreover intended to allocate a timer to said common control part, which brings about a switching-over of said group sound-reproduction stage to said sound-carrier reproducers and back. For example, the timer can make a first switching after completion of the hypnotic introduction after about 20 minutes for about 5 minutes over to individual suggestion and then a back-switching for about 30 minutes to group information for deepening the hypnosis and returning out of the hypnosis.

A light-control means may also be controlled by said timer.

In order to give the therapist the possibility of controlling the sound-carrier reproducers of the headphone stations, they are appropriately arranged in the region of the group sound-reproduction stage. However, this demands an extreme marking or characterization of the devices as to the coordination thereof with the headphone stations in order to avoid confusion of the individual therapy information as much as possible.

It is more advantageous to place the sound-carrier reproducers of the headphone stations there also, which gives the patient the opportunity of having his individual sound carrier with him (additional, positive, suggestive effect) and to place this in "his" station (which puts aside the feeling of an interdiction and increases the sense of self-worth).

Moreover, said individual arrangement permits a subsequent extension of the hypnotic apparatus whenever desired.

BRIEF DESCRIPTION OF THE DRAWING

An embodiment of the multi-functional hypnosis apparatus according to the invention will now be described with reference to the accompanying drawing, the sole FIGURE of which diagrammatically shows the apparatus.

SPECIFIC DESCRIPTION

The multi-functional hypnosis apparatus represented here comprises only two headphone stations 1 and 2 to give therapy to two patients simultaneously. It is to be emphasised, however, that such apparatus may be constructed for practically any desired number of patient stations. As a rule, about 6 to 20 stations will be provided.

The headphone stations 1 and 2, which, for example, may be placed directly at the resting-places for the patients or disposed in side furniture or the like, comprise in each case a headphone 1' or 2' as well as an associated sound-carrier reproducer 11 and 12 with a connected intensifier (amplifier) and modulation stage 11' or 12'. Furthermore, loudspeaker means (not shown) may also be provided.

Commercial CD equipment or tape recorders can serve as sound-carrier reproducers. The headphones, intensifiers and modulation stages as well as said loudspeaker means are of commercial design and, therefore, need no further elucidation.

The headphone stations 1 and 2 or the headphones 1' and 2' thereof are now alternately switchable between said sound-carrier reproducers 11 or 12 thereof and a control part 3, common with both headphone stations 1 and 2, which comprises a sound-producing stage 4 for the introduction of the hypnosis in a group or the deepening thereof or the return out of the hypnosis.

The switching-over is effected appropriately via a timer 15, which alternately connects the sound-reproduction stage 4 via the supply lead 15' or said individual sound-carrier reproducers 11 and 12 via the supply lead 15" to the power network 13. A master switch 14 is disposed upstream of said timer 15. At the same time, said master switch 14 also connects said intensifier and modulation stages 11' or 12', disposed upstream of said individual microphones 1' and 2', via supply lead 14' to said power network 13.

The sound-reproducing stage 4 for group therapy comprises here a sound-carrier reproducer 5 of commercial design as well as a microphone 6, which can be switched on alternately via switch means 7.

The microphone 6 and if necessary also the sound-carrier reproducer 5 are alternately connectable via appropriate switch means with the intensifier stage amplifier 8, with a room loudspeaker 9 or with the connections 10 of said intensifier stage 8 for the previously-mentioned station loudspeaker (not shown) or directly with the headphones 1' and 2' of the stations 1 and 2.

Further, a sound-generating unit 17 for generating the rushing of the sea or the like is allocated to said common control part 3, which is selectively switched on via a switch 16 and is switched over by said timer to said intensifier and moderation stages 11' and 12' of said stations or individual sound-carrier reproducers 11 and 12 or to said sound-reproduction stage 4 for group therapy or a downstream modulation stage 19. Preferably, a controllable, time-controlled threshold stage 18 is downstream of said sound-generating unit 17.

Thus results is a multi-functional hypnosis apparatus that can meet any requirements imposed thereon, and, owing to the utilization of customary devices, intensifier and modulation stages as well as switching-units, can be easily and inexpensively constructed. Thereby, relevant is for any desired station connection, practically only the number of connections and the output power of the intensifiers of the group-side, sound-reproducing stage of the common control part.

Moreover, this apparatus is extendible by means of further sound-carrier reproducers for the central sound-reproduction stage, for instance, for reserves or also for the utilization of subliminal processes. The same also applies with regard to an extension of the apparatus by light-producing and light-influencing as well as resonance- or echo-producing switching arrangements.

I claim:

1. An apparatus for hypnotherapy for a plurality of subjects, comprising:
   a plurality of headphone stations each having:
      a respective headphone for a respective one of said objects,
      a respective individual sound-carrier reproducer for each of said subjects connectable to the respective headphone for generating a hypnotherapy suggestion program individual to the respective subject, and
      a respective intensifier and modulation stage individual to and connected to the respective headphone;
   a control station connected to all of said headphone stations and provided with:
      a sound-reproduction stage connectable to all of said headphone stations and having a common sound-carrier reproducer for initiation, deepening and withdrawal from hypnosis, a microphone and first switch means for selectively connecting said microphone and said common sound-carrier reproducer to said headphone stations,
      second switch means for selectively enabling connection of said sound-reproduction stage and said individual sound-carrier reproducers to the respective headphones, and
      a group-therapy modulation stage between said sound-reproduction stage and said headphone stations;
   a sound-generating unit common to all of said headphone stations for generating a signal representing a rushing-sea sound and provided with means for selectively switching on of said sound-generating unit and for selectively connecting said sound-generating unit to said group-therapy modulation stage and to said intensifier and modulation stages so that said rushing-sea sound can be superimposed on voiced suggestions delivered by said individual sound-carrier reproducers, said common sound-carrier reproducer and said microphone; and
   a timer at said control station for time-control switch-over of said second switch means.

* * * * *